United States Patent
Rix et al.

(12) 
(10) Patent No.: US 6,657,090 B2
(45) Date of Patent: Dec. 2, 2003

(54) PROCESS FOR PREPARING HIGHLY PURE RAFFINATE II AND METHYL TERT-BUTYL ETHER

(75) Inventors: Armin Rix, Marl (DE); Gerda Grund, Duelmen (DE); Wilfried Bueschken, Haltern (DE)

(73) Assignee: Oxeno Olefinchemie GmbH, Marl (DE)

( * ) Notice: Subject to any disclaimer, the term of this patent is extended or adjusted under 35 U.S.C. 154(b) by 0 days.

(21) Appl. No.: 09/981,985

(22) Filed: Oct. 19, 2001

(65) Prior Publication Data

US 2002/0078622 A1 Jun. 27, 2002

(30) Foreign Application Priority Data

Oct. 19, 2000 (DE) .......................... 100 51 812
Jan. 18, 2001 (DE) .......................... 101 02 082

(51) Int. Cl.$^7$ .............................................. C07C 41/09
(52) U.S. Cl. .......................... 568/697; 585/685; 208/16
(58) Field of Search .................... 568/697; 585/685; 208/16

(56) References Cited

U.S. PATENT DOCUMENTS

| | | | |
|---|---|---|---|
| 4,444,648 A | 4/1984 | West | |
| 4,475,005 A | 10/1984 | Paret | 568/697 |
| 4,504,687 A | 3/1985 | Jones, Jr. | |
| 4,570,026 A | 2/1986 | Keyworth et al. | |
| 4,797,133 A | 1/1989 | Pujado | |
| 4,847,430 A * | 7/1989 | Quang et al. | 202/158 |
| 4,847,431 A * | 7/1989 | Nocca et al. | 202/158 |
| 4,950,803 A * | 8/1990 | Smith et al. | 568/697 |
| 5,120,403 A | 6/1992 | Smith, Jr. | |
| 5,244,929 A | 9/1993 | Gottlieb et al. | |
| 5,248,836 A * | 9/1993 | Bakshi et al. | 568/697 |
| 5,368,691 A | 11/1994 | Asselineau et al. | |
| 5,498,318 A * | 3/1996 | Alagy et al. | 203/29 |

FOREIGN PATENT DOCUMENTS

| | | |
|---|---|---|
| EP | 0 428 265 A1 | 5/1991 |
| EP | 0 885 866 A1 | 12/1998 |
| WO | WO 90/02603 | 3/1990 |
| WO | WO 94/15894 | 7/1994 |

OTHER PUBLICATIONS

DeGarmo et al., Consider Reactive Distillation, Chemical Engineering Progress, Mar. 1992, pp. 43–50.*
Hoshang Subawalla and James R. Fair, "Design Guidelines for Solid–Catalyzed Reactive Distillation Systems", Ind. Eng. Chem. Res., vol. 38, pp. 3696–3709, 1999.
Lawrence A. Smith, et al., "Catalytic Distillation", 13$^{th}$ Proc. Inter. Soc. Energy Convers. Conf., vol. 2, pp. 998–1002, 1984.

* cited by examiner

*Primary Examiner*—Rosalynd Keys
(74) *Attorney, Agent, or Firm*—Oblon, Spivak, McClelland, Maier & Neustadt, P.C.

(57) ABSTRACT

The present invention provides a process, which includes:
  contacting at least one $C_4$-hydrocarbon stream which includes isobutene with methanol over at least one acid catalyst and preparing methyl tert-butyl ether (MTBE) and a substantially isobutene-free $C_4$-hydrocarbon mixture; wherein
    in a first stage in one or more first reactors, the isobutene reacts with the methanol over an acid catalyst to form an equilibrium mixture which includes MTBE, remaining isobutene and methanol;
    the equilibrium mixture is fed to a second stage which includes a reactive distillation column; and
    in the reactive distillation column, the remaining isobutene reacts with methanol over an acid ion exchange resin to form MTBE;
wherein the reactive distillation column is operated at a pressure ranging from 3 to 15 bar abs., a reaction zone temperature ranging from 55° C. to 75° C., and a reflux ratio of less than 1. The present invention also provides a method of making gasoline, which includes the above process and contacting the MTBE with a fuel.

18 Claims, 1 Drawing Sheet

US 6,657,090 B2

PROCESS FOR PREPARING HIGHLY PURE RAFFINATE II AND METHYL TERT-BUTYL ETHER

BACKGROUND OF THE INVENTION

1. Field of the Invention

The invention relates to a process for preparing highly pure raffinate II (a $C_4$-hydrocarbon mixture) which has a low isobutene content and is particularly suitable for the preparation of pure 1-butene and methyl tert-butyl ether (MTBE).

2. Discussion of the Background

Isobutene-free butene mixtures are suitable for preparing highly pure 1-butene and/or for preparing butene oligomers having a low degree of branching. MTBE is a sought-after carburetor fuel component for increasing the octane number. For this purpose, there is no harm if other ethers such as methyl sec-butyl ether or oligomers of $C_4$-olefins are present in the MTBE. High-purity MTBE which is to be used as a solvent, however, requires significantly tighter limits for the abovementioned secondary components.

MTBE and linear butenes are obtained from $C_4$-olefin mixtures, for example the $C_4$ fraction from steam crackers or FCC units. These mixtures include or consist essentially of butadiene, the monoolefins isobutene, 1-butene and the two 2-butenes together with the saturated hydrocarbons isobutane and n-butane. Customary work-up methods used worldwide for such $C_4$ fractions include the following steps: first, the major part of the butadiene is removed. If butadiene can be readily marketed or there is a use for it within the company, it is separated off, for example by extraction or extractive distillation. Otherwise, it is hydrogenated selectively to linear butenes so as to leave butadiene concentrations of from 1 to 0.1%. In both cases, a hydrocarbon mixture (corresponding to raffinate I or hydrogenated crack-$C_4$) that includes the saturated hydrocarbons (n-butane and isobutane) together with the olefins (isobutene, 1-butene and 2-butenes) remains. A possible way of removing the isobutene from this mixture is reaction with methanol to form MTBE. This leaves the saturated hydrocarbons, linear butenes and possibly a residual amount of isobutene. The $C_4$ mixture obtained after removal of the butadiene and isobutene is referred to as raffinate II.

Depending on the further use of the two streams (MTBE and the olefin mixture, raffinate II), particular qualities of these streams are of special interest. If the isobutene from the $C_4$ fraction is utilized for producing carburetor fuel components (be it as MTBE or oligomer), the purity of the MTBE is not subject to any critical requirements. Other ethers such as methyl sec-butyl ether and/or $C_4$-olefin oligomers can be present in the MTBE.

In addition to the linear olefins, relatively large amounts of isobutene can be present in raffinate II if this $C_4$ mixture is reacted, for example, over acid catalysts, to form mostly branched $C_4$-oligomers, in particular $C_8$- and $C_{12}$-oligomers. After hydrogenation, this mixture gives a high-octane carburetor fuel component.

If the MTBE is to be used, for example, as a pure solvent or for preparing highly pure isobutene in a cleavage reaction, it is allowed to contain only small amounts of secondary components. The synthesis to form MTBE therefore has to be carried out very selectively. If the raffinate II is to be used for preparing oligomers having low iso indices, i.e. a low degree of branching, the isobutene content has to be very low, preferably less than 1000 ppm by weight. Virtually isobutene-free raffinate II is necessary if pure 1-butene is to be obtained from this raffinate II. The isobutene concentration of the raffinate II should then not exceed 450 ppm by weight. Since the boiling point difference between isobutene and 1-butene is only 0.6° C., economical separation of the two components by distillation is not possible. In this case, isobutene has to be reacted virtually completely in the MTBE synthesis.

The highest demands are placed on the MTBE synthesis if solvent-quality MTBE is to be produced and the raffinate II is at the same time to be used for 1-butene production. Here, both a very high isobutene conversion and a very high MTBE selectivity are necessary.

The preparation of MTBE from isobutene-containing $C_4$-hydrocarbon mixtures such as raffinate I or hydrogenated crack-$C_4$ by reaction with methanol is frequently carried out industrially using acid ion exchange resins (sulfonic acid groups) as heterogeneous catalysts. The reaction is carried out in one or more reactors connected in series, with the catalyst preferably being present as a fixed bed. This gives a product in which methanol, isobutene and MTBE are in equilibrium. The equilibrium conversion is established in each reactor as a function of the reaction conditions (temperature, methanol excess, etc.). This means that under the reaction conditions customarily set in industrial processes, about 96% of the isobutene used is reacted. This mixture can subsequently be fractionally distilled to give a bottom fraction containing MTBE and a top fraction containing $C_4$-hydrocarbons and methanol. After removal of the methanol present as an azeotrope, the raffinate II produced in this way is not suitable for producing pure 1-butene because of its high residual isobutene content.

To obtain virtually complete isobutene conversion, reactive distillation columns are used in industry. These are columns which contain both separation trays (or mesh packing) and catalysts on separation trays or integrated into other internals or mesh packing. In such columns, the reaction of the residual isobutene with methanol to form MTBE and the separation of the products by distillation occur simultaneously. The feed olefin mixture, for example raffinate I or selectively hydrogenated crack-$C_4$, can also be fed into such a column. These columns are particularly useful for the abovementioned equilibrium mixture in order to achieve very high conversions. Products obtained are an azeotrope containing methanol and $C_4$-hydrocarbons, which in the case of 1-butene production has to be virtually free of isobutene, at the top and MTBE at the bottom.

U.S. Pat. No. 4,504,687 describes a process for preparing MTBE and a low-isobutene $C_4$ stream. Here, the reaction of a $C_4$ stream containing both isobutene and linear butenes with methanol is carried out in a reactive distillation column in which reaction and distillation are, due to structural measures, carried out at different pressures. The division of the column in terms of pressure into a distillation section and a reaction section is structurally complicated. No information is given on the purity of the products prepared in U.S. Pat. No. 4,504,687. A large reflux ratio of 0.5–20:1 is disclosed for the reactive distillation column.

In U.S. Pat. No. 5,120,403, the same reaction is carried out in a reactive distillation column in which the catalyst is flooded. Although the reaction to form MTBE can proceed more readily in a liquid phase, the distillation is made more difficult, as a result of which the separation of the components to produce highly pure products is not ensured.

EP 0 885 866 A1 discloses a process in 6 embodiments for preparing MTBE and a low-isobutene $C_4$ stream by reacting a $C_4$-hydrocarbon stream containing isobutene and n-butenes with methanol. The feature common to all embodiments is that at least one prereactor, a reactive distillation column and an after-reactor are connected in series.

In all three abovementioned publications, neither the quality of the MTBE prepared nor the isobutene content of the remaining $C_4$ stream is disclosed.

U.S. Pat. No. 5,368,691 describes the reaction of a $C_4$-hydrocarbon mixture containing isobutene and linear butenes with methanol to form MTBE and a $C_4$ stream containing the linear butenes in a reactive distillation column. Here, MTBE is obtained as bottom product in a purity of greater than 98%, which does not meet the requirements for the preparation of solvent-quality MTBE. The example describes a top product having a residual isobutene content of 1.4%. This isobutene content is far too high for further processing to produce pure 1-butene. The reflux ratio of the column is stated to be from 0.5:1 to 5:1.

A further process for preparing MTBE and a low-butene $C_4$ stream using a reactive distillation column is described in U.S. Pat. No. 4,475,005. Here, the column is operated at a reflux ratio of 1. The isobutene content of the distillate is 4830 ppm by weight and is thus significantly too high for further use for producing pure 1-butene.

Since the known processes are not fully satisfactory in respect of the isobutene content of the top product or of the raffinate II produced therefrom and/or the quality of the MTBE obtained and/or capital cost and/or energy consumption, it is desirable to develop a process which produces a raffinate II which is suitable for cost-effective production of 1-butene and at the same time gives MTBE in solvent quality.

SUMMARY OF THE INVENTION

One object of the invention is to develop a process which produces a raffinate II which is suitable for cost-effective production of 1-butene.

Another object of the invention is to develop a process which produces a raffinate II which is suitable for cost-effective production of 1-butene and at the same time gives MTBE in solvent quality.

It has surprisingly been found that the acid-catalyzed reaction of methanol and a $C_4$-olefin mixture in a two-stage plant with a reactive distillation column as second stage makes it possible to obtain an overall isobutene conversion of above 99.9% and a virtually isobutene-free raffinate II and at the same time gives an MTBE which contains virtually no impurities if specific reaction conditions in terms of reflux ratio, temperature and pressure are adhered to in the reactive distillation column.

Thus, one embodiment of the present invention provides a process, which includes:
    contacting at least one $C_4$-hydrocarbon stream including isobutene with methanol over at least one acid catalyst and preparing methyl tert-butyl ether (MTBE) and a substantially isobutene-free $C_4$-hydrocarbon mixture; wherein
        in a first stage in one or more first reactors, the isobutene reacts with the methanol over an acid catalyst to form an equilibrium mixture including MTBE, remaining isobutene and methanol;
        the equilibrium mixture is fed to a second stage including a reactive distillation column; and
        in the reactive distillation column, the remaining isobutene reacts with methanol over an acid ion exchange resin to form MTBE;
    wherein the reactive distillation column is operated at a pressure ranging from 3 to 15 bar abs., a reaction zone temperature ranging from 55° C. to 75° C., and a reflux ratio of less than 1.

Another embodiment of the present invention provides a method of making gasoline, which includes the above process and contacting the MTBE with a fuel, to obtain gasoline.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
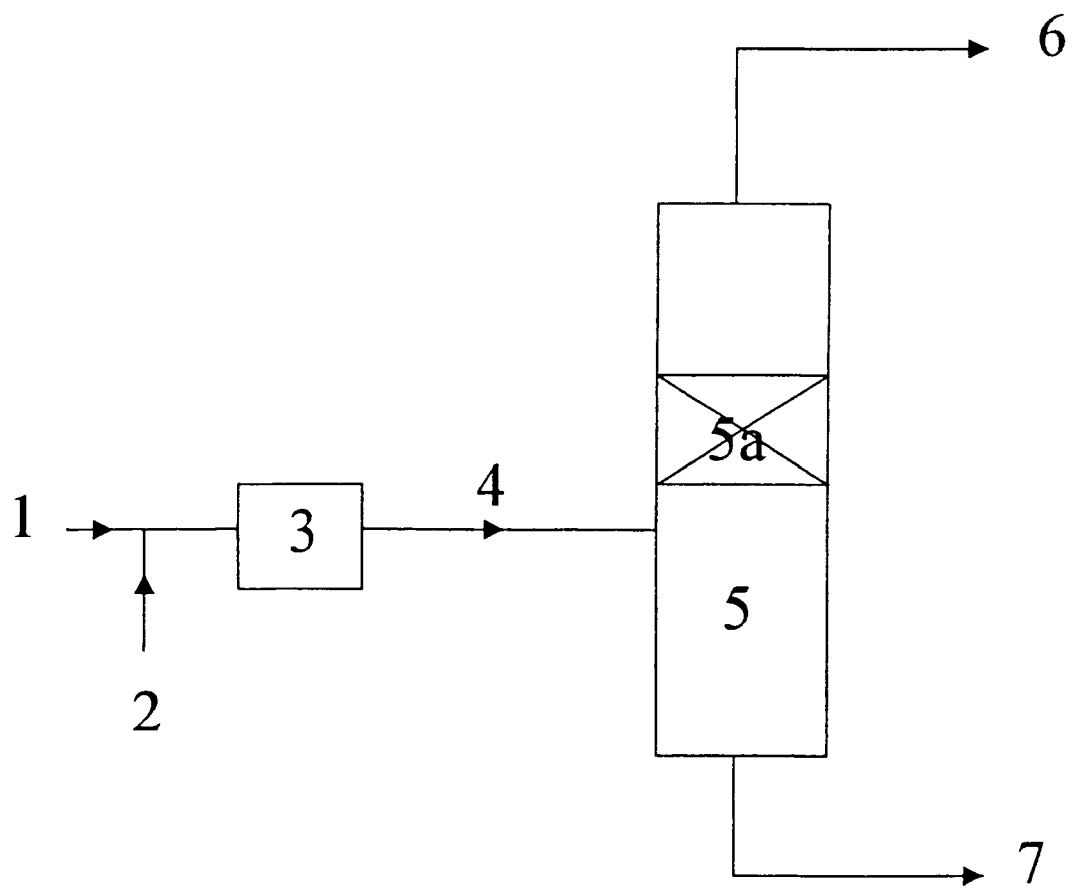
FIG. 1 shows a block diagram of a plant in which the process of the invention can be carried out.

Various other objects, features and attendant advantages of the present invention will be more fully appreciated as the same becomes better understood from the following detailed description of the preferred embodiments of the invention.

A preferred embodiment of the invention provides a process for preparing methyl tert-butyl ether (MTBE) and a virtually isobutene-free $C_4$-hydrocarbon mixture, which includes reaction of an isobutene-containing $C_4$-hydrocarbon stream with methanol over an acid catalyst, wherein, in a first stage in one or more reactor(s), isobutene is reacted with methanol to equilibrium formation of MTBE and, in a second stage in a reactive distillation column, the remaining isobutene present in the mixture is reacted over an acid ion exchange resin, where the reactive distillation column is operated in a pressure range from 3 to 15 bar abs. and in a temperature range in the reaction zone from 55° C. to 75° C. at a reflux ratio of less than 1. Owing to the high conversion, the product obtained at the top contains less than 450 ppm by weight of isobutene and is therefore very suitable for the production of pure 1-butene. The MTBE produced has a purity which enables it to be used as solvent.

The reflux ratio is defined as the ratio (by volume or weight) of the reflux stream in the column to the distillate stream taken off.

This finding that a better isobutene conversion is obtained at low reflux ratios and temperatures in the catalyst packing than at higher reflux ratios is surprising, since the opposite is described in the literature.

For example, it is shown in the following publications that, similar to the case of a distillation, the reaction rate of the reaction of the isobutene-containing $C_4$ streams with methanol to form MTBE in a reactive distillation column rises with increasing reflux ratio (Lawrence A. Smith, D. Hearn, Catalytic Destillation, Proc. Intersoc. Energy Convers. Conf. (1984) 19th, (Vol 2), p 998–1002; Miguel A. Isla, Horazio A. Irazoqui, Modeling, Analysis, and Simulation of a Methyl tert-Butyl Ether Reactive Destillation Column, Ind. Eng. Chem. Res. 1966, 35, 2696–2708; Hoshang Subawalla, James R. Fair, Design Guideline for Solid-Catalyzed Distillation Systems, Ind. Eng. Chem. Res. 1999, 38, 3696–3709, or in "Rate-Based Modeling of Reactive Destillation Systems", V. Pinjala and T. L. Marker et al., Topical Conference on Separations Technologies ATChE, 1–6, 11. 1992). Setting a low reflux ratio in accordance with the present invention is therefore contrary to the teachings of the above references. The process of the invention has a series of advantages, which are unexpected and surprising. The process makes it possible to obtain a distillate containing less than 450 ppm by weight of isobutene based on the $C_4$-hydrocarbons and/or containing less than 0.5 ppm by weight of MTBE (except for methanol) and is thus suitable for producing pure 1-butene containing less than 1000 ppm by weight of isobutene. The MTBE is of such high quality that it can be utilized both as precursor for the preparation of high-purity isobutene and as solvent.

The lowering of the reflux ratio also leads to a significant steam saving, as a result of which the process of the invention has a low energy requirement.

In the present context, the term substantially isobutene-free $C_4$-hydrocarbon mixture contains less than 450 ppm by weight of isobutene based on the weight of the $C_4$-hydrocarbons. This range includes all values and subranges therebetween, including 425, 400, 350, 325, 300, 250, 200, 150, 100, 50, 25, 10, 1, 0.75, 0.5 and 0 ppm.

In the process of the invention, the reaction of isobutene with methanol to form MTBE is carried out in two stages (see FIG. 1). The first stage includes the reaction of isobutene in the $C_4$ mixture with methanol in one or more reactors until thermodynamic equilibrium between MTBE, methanol and isobutene has been established. This is generally at an isobutene conversion of from 94 to 96%. The reactors of the first stage can be conventional fixed-bed reactors containing the same catalysts as are described below for the second stage. The reactors are usually operated at 30–110° C. and 5–50 bar abs. These ranges include all values and subranges therebetween, including 35, 40, 45, 50, 60, 70, 80, 90, 100 and 105° C., and 10, 15, 20, 25, 30, 35, 40 and 45 bar abs.

Preferred compositions of the reaction mixtures obtained in this way are described in the examples. In general, these mixtures contain less than 1% by weight of isobutene which is reacted very selectively to form MTBE in the subsequent second stage, viz. the reactive distillation column.

The catalyst is present in the enrichment section of this reactive distillation column, and separation trays or distillation packing are/is present below and above the catalyst packing. The catalyst is either integrated into a packing unit, for example KataMax® (EP 0 428 265), KataPak® (EP 0 396 650) or MultiPak® (utility model No. 298 7 007.3), or polymerized onto shaped bodies (U.S. Pat. No. 5,244,929). The entire contents of each of the aforementioned patents, applications and published applications is hereby incorporated by reference.

The zone above the catalyst packing includes from 5 to 20 theoretical plates, in particular from 10 to 15 theoretical plates. The catalyst zone can be estimated as having a distillation efficiency of from 1 to 5 theoretical plates per meter of packing height. The separation zone below the catalyst includes from 12 to 36 theoretical plates, in particular from 20 to 30 theoretical plates. These respective ranges include all values and subranges therebetween, including 6, 7, 8, 9, 11, 13, 17, and 19 theoretical plates (in the zone above the packing); 11, 12, 13 and 14 theoretical plates per meter of packing height; and 13, 15, 17, 19, 21, 23, 25, 27, 29, 31, 33 and 35 theoretical plates (in the separation zone below the catalyst).

The actual catalyst used in the two stages of the process is a solid which is soluble neither in the feed mixture nor in the product mixture and has acid centers on its surface. Most preferably, the catalyst must not release any acidic substances into the product mixture under reaction conditions, because this would lead to yield losses.

Most preferably, the activity of the catalysts must be such that, under reaction conditions, they effect the addition of methanol onto isobutene but do not bring about addition onto linear butenes to a significant extent. Furthermore, and more preferably, the catalysts must not catalyze the oligomerization of olefins and the formation of dimethyl ether to any significant extent.

A preferred group of acid catalysts which can be used in the process of the invention are solid ion exchange resins containing sulfonic acid groups. Suitable ion exchange resins include, for example, ones prepared by sulfonation of phenol/aldehyde condensates or cooligomers of aromatic vinyl compounds. Examples of aromatic vinyl compounds for preparing the cooligomers are: styrene, vinyltoluene, vinylnaphthalene, vinylethylbenzene, methylstyrene, vinylchlorobenzene, vinylxylene and divinylbenzene. Particular preference is given to using the cooligomers formed by reaction of styrene with divinylbenzene as precursors for the preparation of ion exchange resins containing sulfonic acid groups. The resins produced can be in gel form, macroporous or in sponge form. Strong acid resins of the styrene-divinyl type are sold, inter alia, under the following trade names: Duolite C20, Duolite C26, Amberlyst A15, Amberlyst A35, Amberlite IR-120, Amberlite 200, Dowex 50, Lewatit SPC 118, Lewatit SPC 108, K2611, K2621, OC 1501. Mixtures of catalysts are possible.

The properties of these resins, in particular specific surface area, porosity, stability, swelling or shrinkage and ion exchange capacity, are not particularly limited and can be varied by means of the production process.

In the process of the invention, the ion exchange resins can be used in their H form. Preference is given to using macroporous resins, for example Lewatit SCP 118, Lewatit SCP 108, Amberlyst A15 or Amberlyst A35, K2621. The pore volume is from 0.3 to 0.9 ml/g, in particular from 0.5 to 0.9 ml/g. The particle size of the resin is from 0.3 mm to 1.5 mm, in particular from 0.5 mm to 1.0 mm. The particle size distribution selected can be relatively narrow or relatively broad. Thus, for example, ion exchange resins having a very uniform particle size (monodisperse resins) can be used. The capacity of the ion exchanger is, based on the product as supplied, 0.7–2.0 mol/l, in particular 1.1–2.0 mol/l.

The abovementioned ranges include all values and subranges therebetween, including independently 0.4, 0.45, 0.55, 0.6, 0.7, 0.8, and 0.85 ml/g (pore volume); 0.4, 0.6, 0.7, 0.8, 0.9, 1, 1.1, 1.2, 1.3 and 1.4 mm (particle size of the resin); and 0.8, 0.9, 1.0, 1.2, 1.3, 1.5, 1.7 and 1.9 mol/l (capacity of the ion exchanger).

Preferable feedstocks which can be used for the process of the invention are $C_4$-hydrocarbon mixtures containing both isobutene and linear butenes, but no acetylene derivatives and less than 8000 ppm by weight of butadiene. Examples of industrial mixtures which may contain both isobutene and linear butenes are light gasoline fractions from refineries, $C_4$ fractions from FCC units or steam crackers, mixtures from Fischer-Tropsch syntheses, mixtures from dehydrogenation of butanes, mixtures from skeletal isomerization of linear butenes, mixtures formed by metathesis of olefins or other industrial processes.

After removal of multiply unsaturated compounds, these mixtures can be used in the process of the invention. For example, a suitable feed mixture can be obtained from the $C_4$ fraction from a steam cracker by extraction of the butadiene or by selective hydrogenation of the butadiene to linear butenes. This mixture (raffinate I or selectively hydrogenated crack-$C_4$) includes n-butane, isobutane, the three linear butenes and isobutene and is a preferred starting material for the process of the invention.

The hydrocarbon feed mixture can be fed together with methanol into the first stage of the process. Catalysts used are the same catalysts as those used in the reactive distillation column or catalysts similar to these. The first stage produces a mixture in which isobutene, methanol and MTBE are in equilibrium. A preferred embodiment of the process of the invention includes producing an equilibrium mixture or a mixture close to equilibrium in the first stage and feeding it to the reactive distillation column (second stage).

The feed to the column of the second stage can contain more methanol than is required for complete reaction of the remaining isobutene. However, the methanol excess should preferably be limited so that, on the one hand, a sufficient amount of methanol for the azeotrope formed from methanol and $C_4$-hydrocarbons is present but, on the other hand, not so much that methanol gets into the bottom product, so that an MTBE which meets specifications (methanol content less than 5000 ppm by weight) is obtained.

If the methanol content in the feed to the column is below the maximum permissible value, additional methanol may, if appropriate, be introduced into the feed mixture before it is fed into the column. Furthermore, methanol can be fed in at the top of the reactive distillation column via a separate facility.

The temperature of the feed to the column is, regardless of its composition, the reaction pressure in the column and the throughput, from 50° C. to 80° C., preferably from 60° C. to 75° C. These ranges include all values and subranges therebetween, including 55, 65 and 70° C.

The mean temperature in the catalyst zone is, depending on the pressure in the column, preferably from 55° C. to 70° C., particularly preferably from 58° C. to 67° C. These ranges include all values and subranges therebetween, including 56, 57, 59, 60, 62, 65, and 69° C.

The reactive distillation column is operated at pressures, measured at the top of the column, of 3–15 bar abs., preferably from 5 bar abs. to 9 bar abs., in particular from 7 bar abs. to 8.5 bar abs. These ranges include all values and subranges therebetween, including 4, 6, 7.5, 8, 9.5, 10, 12 and 14 bar abs.

The hydraulic loading in the catalyst packing of the column is preferably from 10% to 110%, more preferably from 20% to 70%, of its flooding point loading. These ranges include all values and subranges therebetween, including 15, 25, 35, 45, 55, 65, 75, 85, 95 and 100%. For the purposes of the present invention, hydraulic loading of a distillation column is the uniform hydrodynamic loading of the column cross section by the rising stream of vapor and the downflowing stream of liquid. The upper loading limit is the maximum loading by vapor and downflowing liquid above which the separation efficiency drops as a result of entrainment or backing-up of the downflowing liquid by the rising stream of vapor. The lower loading limit is the minimum loading below which the separation efficiency decreases or breaks down as a result of irregular flow or empty running of the column, e.g. the trays. (Vauck/Müller, "Grundoperationen chemischer Verfahrenstechnik", p. 626, VEB Deutscher Verlag für Grundstoffindustrie., the entire contents of which are hereby incorporated by reference.)

At the flooding point, the shear stresses transmitted from the gas to the liquid become so great that the entire liquid is entrained in the form of droplets in the gas and carried along with it or phase inversion occurs in the column (J. Mackowiak, "Fluiddynamik von Kolonnen mit modernen Füllkörpern und Packungen für Gas/Flüissigkeitssysteme", Otto Salle Verlag 1991, the entire contents of which are hereby incorporated by reference.).

In the process of the invention, the column is operated at reflux ratios of less than 1, in particular reflux ratios which are greater than 0.6 and less than 1, preferably in the range from 0.7 to 0.9. These ranges include all values and subranges therebetween, including 0.2, 0.3, 0.4, 0.5 and 0.8.

At these reflux ratios, residual isobutene concentrations in the raffinate II of less than 450 ppm by weight, preferably less than 400 ppm by weight, very particularly preferably less than 300 ppm by weight (based on the $C_4$ mixture in the distillate), are obtained according to the invention. The optimum reflux ratio depends on the throughput, the composition of the feed to the column and the column pressure. However, it is always within the abovementioned ranges. This range includes all values and subranges therebetween, including 425, 400, 350, 325, 300, 250, 200, 150, 100, 50, 25, 10, 1, 0.75, 0.5 and 0 ppm.

Optionally, a top product containing a $C_4$-hydrocarbon mixture and methanol and having an isobutene content of less than 450 ppm by weight, preferably less than 400 ppm by weight, very particularly preferably less than 300 ppm by weight, and a bottom product containing MTBE and having a methyl sec-butyl ether (MSBE) content of less than 2500 ppm by weight can be obtained in the second stage of the process. These ranges include all values and subranges therebetween, including independently 425, 400, 350, 325, 300, 250, 200, 150, 100, 50, 25, 10, 1, 0.75, 0.5 and 0 ppm (isobutene in the top product); 2400, 2000, 1500, 1100, 800, 750, 600, 550, 100, 50, 10, 1, and 0 ppm (MSBE in the bottom product).

The top product can in turn be separated into a $C_4$-hydrocarbon mixture and methanol, with the $C_4$-hydrocarbon mixture containing less than 0.5 ppm by weight of MTBE and/or TBA.

The bottom product from the reactive distillation column preferably includes MTBE and less than 2500 ppm by weight of methyl sec-butyl ether and less than 2500 ppm by weight of $C_8$-hydrocarbons. Further purification of the MTBE is no longer necessary if it is to be used as a component of gasoline such as 4-stroke and 2-stroke fuels.

The methanol can be separated off from the top product by, for example, extraction with water. Traces of butadiene can be removed from the resulting raffinate II by selective hydrogenation (SHP). This mixture can be fractionally distilled to give 1-butene, isobutane and a mixture of 2-butenes and n-butane or to give 1-butene, 2-butene and n-butane.

The pure 1-butene produced in this way contains less than 1000 ppm by weight of isobutene and is a sought-after intermediate. It is used, for example, as comonomer in the production of polyethylene (LLDPE or HDPE) and of ethylene-propylene copolymers. It is also used as alkylating agent and is a starting material for the preparation of 2-butanol, butene oxide, valeraldehyde.

A further use of the virtually isobutene-free raffinate II produced according to the invention is the preparation of n-butene oligomers, in particular by the Octol process.

The hydrocarbons which remain after removal or reaction of the linear butenes in the raffinate II can, if desired, be worked up by hydrogenation (CSP) to give isobutane and n-butane.

The MTBE obtained as bottom product from the reactive distillation column can be used for various purposes. Since it contains only extremely small amounts of methyl sec-butyl ether (MSBE), it is suitable for the preparation of highly pure isobutene by cleavage, since virtually no linear butenes can be formed (by cleavage of methyl sec-butyl ether). The cleavage of MTBE can be carried out as described in, for example, DE 100 20 943.2, the entire contents of which are hereby incorporated by reference.

Owing to its low content of by-products (MSBE and $C_8$-olefins), the MTBE obtained in this way can, after removal of the residual alcohols, be used as solvent in analysis or in organic syntheses.

It is also possible for it to be used as a component of 4-stroke and 2-stroke fuels.

A block diagram of a plant in which the process of the invention can be carried out is shown in FIG. 1.

A $C_4$-hydrocarbon mixture (raffinate I or selectively hydrogenated crack-$C_4$) (1) is reacted with methanol (2) in the reactor (3) in which an acid ion exchange resin is present to give an MTBE-containing reaction mixture (4) which is fed into a reactive distillation column (5) at a point below the catalyst packing (5a). As top product (6), methanol and a $C_4$ stream containing less than 300 ppm by weight of isobutene is obtained. MTBE is taken off as bottom product (7).

EXAMPLES

Having generally described this invention, a further understanding can be obtained by reference to certain specific examples which are provided herein for purposes of illustration only and are not intended to be limiting unless otherwise specified.

Example 1 (Comparative Example)

The reaction of the $C_4$ mixture having the composition indicated in Table 1 was carried out in a reactive distillation column (see FIG. 1) which was provided with Amberlyst A15 in KATAMAX packing. The packing was located in the upper part of the column. Above the feed point there are separation trays, followed by three KATAMAX packings each having a liquid distributor, and finally more distillation trays. Below the feed point, there are appropriately dimensioned stripping sections in order to bring about the separation of MTBE from $C_4$-hydrocarbons.

The column was operated at a pressure at the top of 8.2 bar abs., temperatures in the packing units, in order from the feed tray upward, of 65.8° C., 65.4° C. and 65.1° C., at a hydraulic loading of the catalyst packing of 36% and a reflux ratio of 1.02. When the reactive distillation column was operated in this way, an isobutene conversion in the column of 93.4% was obtained—not enough to achieve the necessary residual isobutene concentration in the raffinate (see analyses in Table 1B).

TABLE 1A

Composition of the streams to/from the reactive distillation column

| | Feed (% by weight) | Distillate (% by weight) | Bottoms (% by weight) |
|---|---|---|---|
| $C_4$-hydrocarbon mixture* | 58.93 | 94.14 | 0.13 |
| MTBE | 37.02 | 0 | 98.00 |
| MSBE | 0.04 | 0 | 0.32 |
| Methanol | 3.68 | 5.86 | 0.57 |
| TBA | 0.29 | 0 | 0.60 |

TABLE 1A-continued

Composition of the streams to/from the reactive distillation column

| | Feed (% by weight) | Distillate (% by weight) | Bottoms (% by weight) |
|---|---|---|---|
| $C_8$ | 0.04 | 0 | 0.27 |
| Others | 0 | 0 | 0.11 |

TABLE 1B

Distribution of $C_4$-hydrocarbons in the mixture* in the feed and distillate to/from the column (in each case normalized to 100%)

| | Feed (% by weight) | Distillate (% by weight) |
|---|---|---|
| Isobutane | 4.79 | 6.00 |
| n-butane | 14.46 | 14.32 |
| trans-2-butene | 23.66 | 24.56 |
| 1-butene | 44.92 | 43.335 |
| Isobutene | 0.68 | 0.048 |
| cis-2-butene | 10.99 | 11.40 |
| 1,3-butadiene | 0.50 | 0.34 |

Example 2

According to the Invention

The reactive distillation column was operated under the same pressure (8.2 bar abs.), temperatures in the packing of 66.5° C., 66.2° C. and 65.8° C., the same hydraulic loading in the catalytic packing of 36% and a composition of the feed stream comparable to that in Example 1. However, the reflux ratio in the column was reduced to 0.89. Tables 2A and 2B show the composition of the streams and allow conversion and selectivity to be derived.

TABLE 2A

Composition of the streams to/from the reactive distillation column

| | Feed (% by weight) | Distillate (% by weight) | Bottoms (% by weight) |
|---|---|---|---|
| $C_4$-hydrocarbon mixture* | 61.471 | 93.88 | 0.17 |
| MTBE | 34.82 | 0 | 98.04 |
| MSBE | 0.04 | 0 | 0.31 |
| Methanol | 3.41 | 6.12 | 0.48 |
| TBA | 0.22 | 0 | 0.62 |
| $C_8$ | 0.039 | 0 | 0.23 |
| Others | 0 | 0 | 0.15 |

TABLE 2B

Distribution of $C_4$-hydrocarbons in the mixture* in the feed and distillate to/from the column

| | Feed (% by weight) | Distillate (% by weight) |
|---|---|---|
| Isobutane | 5.426 | 5.798 |
| n-butane | 13.549 | 13.861 |
| trans-2-butene | 25.733 | 26.138 |
| 1-butene | 42.383 | 42.004 |
| Isobutene | 0.720 | 0.018 |
| cis-2-butene | 11.880 | 11.906 |
| 1,3-butadiene | 0.309 | 0.275 |

Compared to Example 1, Example 2 shows the advantageous effect of reducing the reflux ratio from 1.02 to 0.89.

In Example 2, the isobutene concentration of the distillate is 0.018%, based on the $C_4$-hydrocarbons. This distillate is, in contrast to the distillate from Example 1, suitable for producing 1-butene containing less than 1000 ppm by weight of isobutene.

Example 3

According to the Invention

The reactive distillation column was operated at a pressure of 7.4 bar abs., temperatures in the packing units of 62.2° C., 62.0° C. and 61.6° C., at a hydraulic loading in the catalytic packing of 37% and a reflux ratio of 0.89. Tables 3A and 3B show the composition of the streams to/from the column.

TABLE 3A

Composition of the streams to/from the reactive distillation column

|  | Feed (% by weight) | Distillate (% by weight) | Bottoms (% by weight) |
| --- | --- | --- | --- |
| $C_4$-hydrocarbon mixture* | 61.77 | 95.4 | 0.11 |
| MTBE | 34.84 | 0 | 98.49 |
| MSBE | 0.04 | 0 | 0.21 |
| Methanol | 3.06 | 4.6 | 0.32 |
| TBA | 0.19 | 0 | 0.51 |
| $C_8$ | 0.04 | 0 | 0.19 |
| Others | 0.06 | 0 | 0.17 |

TABLE 3B

Distribution of $C_4$-hydrocarbons in the mixture* in the feed and distillate to/from the column

|  | Feed (% by weight) | Distillate (% by weight) |
| --- | --- | --- |
| Isobutane | 5.271 | 5.576 |
| n-butane | 15.088 | 15.350 |
| Trans-2-butene | 24.589 | 24.335 |
| 1-butene | 42.185 | 43.107 |
| Isobutene | 0.709 | 0.018 |
| cis-2-butene | 11.925 | 11.393 |
| 1,3-butadiene | 0.233 | 0.221 |

Example 3 shows that, at the same reflux ratio as in Example 2, reducing the pressures in the catalyst packing units lowered the concentration of methyl sec-butyl ether (MSBE) in the bottom product without increasing the isobutene content of the distillate. A bottom product of this quality is suitable for producing MTBE of solvent quality.

Obviously, numerous modifications and variations of the present invention are possible in light of the above teachings. It is therefore to be understood that within the scope of the appended claims, the invention may be practiced otherwise than as specifically described herein.

This application is based on German patent applications DE 100 51 812.5, filed Oct. 19, 2000, and DE 101 02 082.1, filed Jan. 18, 2001, the entire contents of each of which are hereby incorporated by reference, the same as if set forth at length.

What is claimed is:

1. A process, comprising:
   contacting at least one $C_4$-hydrocarbon stream comprising isobutene with methanol over at least one acid catalyst and preparing methyl tert-butyl ether (MTBE) and a substantially isobutene-free $C_4$-hydrocarbon mixture; wherein
   in a first stage in one or more first reactors, said isobutene reacts with said methanol over an acid catalyst to form an equilibrium mixture comprising MTBE, remaining isobutene and methanol;
   said equilibrium mixture is fed to a second stage comprising a reactive distillation column; and
   in said reactive distillation column, said remaining isobutene reacts with methanol over an acid ion exchange resin to form MTBE;
   wherein said reactive distillation column is operated at a pressure ranging from 3 to 15 bar abs., a reaction zone temperature ranging from 55° C. to 75° C., and a reflux ratio of less than 1.

2. The process as claimed in claim 1, wherein the reflux ratio is greater than 0.6 and less than 1.

3. The process as claimed in claim 1, wherein, in the second stage, a top product comprising methanol and the $C_4$-hydrocarbon mixture and having an isobutene content of less than 450 ppm by weight, based on the weight of the $C_4$-hydrocarbon mixture, is obtained.

4. The process as claimed in claim 1, wherein the reaction zone temperature ranges from 55° C. to 70° C.

5. The process as claimed in claim 1, wherein the pressure ranges from 7 bar abs. to 8.5 bar abs.

6. The process as claimed in claim 1, wherein said reactive distillation column comprises catalytic packing and is operated at a hydraulic loading of the catalytic packing of from 10% to 110%.

7. The process as claimed in claim 1, wherein, in the second stage, a top product comprising methanol and the $C_4$-hydrocarbon mixture and having an isobutene content of less than 450 ppm by weight, based on the weight of the $C_4$-hydrocarbon mixture, and a bottom product comprising MTBE and having a methyl sec-butyl ether (MSBE) content of less than 2500 ppm by weight are obtained.

8. The process as claimed in claim 7, further comprising separating the $C_4$-hydrocarbon mixture and methanol from the top product.

9. The process as claimed in claim 7, wherein the $C_4$-hydrocarbon mixture contains less than 0.5 ppm by weight of MTBE.

10. The process as claimed in claim 7, wherein the bottom product contains less than 2500 ppm by weight of MSBE and less than 2500 ppm by weight of $C_8$-hydrocarbons.

11. The process as claimed in claim 1, further comprising producing 1-butene from said substantially isobutene-free $C_4$-hydrocarbon mixture.

12. The process as claimed in claim 1, further comprising producing n-butene oligomers from said substantially isobutene-free $C_4$-hydrocarbon mixture.

13. The process as claimed in claim 1, further comprising producing high purity isobutene from said MTBE.

14. The process as claimed in claim 1, further comprising solvating a solute with said MTBE.

15. The process as claimed in claim 1, further comprising preparing gasoline by contacting said MTBE with a fuel.

16. The process as claimed in claim 15, wherein said gasoline is a 4-stroke fuel or a 2-stroke fuel.

17. A method of making gasoline, comprising the process as claimed in claim 1 and contacting said MTBE with a fuel, to obtain gasoline.

18. The method as claimed in claim 17, wherein said gasoline is a 4-stroke fuel or a 2-stroke fuel.

* * * * *